(12) United States Patent
Gaffney et al.

(10) Patent No.: US 10,221,118 B2
(45) Date of Patent: Mar. 5, 2019

(54) ETHER BLENDS VIA REACTIVE DISTILLATION

(71) Applicant: GAS TECHNOLOGIES LLC, Walloon Lake, MI (US)

(72) Inventors: Ian Lawrence Gaffney, Los Gatos, CA (US); Evan Michael Visser, Hull, IA (US); Krishna K. Rao, The Woodlands, TX (US); Walter Breidenstein, Boyne Falls, MI (US)

(73) Assignee: GAS TECHNOLOGIES LLC, Walloon Lake, MI (US)

( * ) Notice: Subject to any disclaimer, the term of this patent is extended or adjusted under 35 U.S.C. 154(b) by 0 days.

(21) Appl. No.: 15/660,149

(22) Filed: Jul. 26, 2017

(65) Prior Publication Data

US 2017/0320801 A1    Nov. 9, 2017

Related U.S. Application Data

(60) Division of application No. 14/777,022, filed as application No. PCT/US2014/028368 on Mar. 14, (Continued)

(51) Int. Cl.
*C07C 41/42* (2006.01)
*B01J 8/02* (2006.01)
(Continued)

(52) U.S. Cl.
CPC .............. *C07C 41/42* (2013.01); *B01D 3/009* (2013.01); *B01J 8/02* (2013.01); *B01J 12/00* (2013.01);
(Continued)

(58) Field of Classification Search
CPC .......... C07C 41/09; C07C 41/42; C07C 29/50; B01J 8/02
See application file for complete search history.

(56) References Cited

U.S. PATENT DOCUMENTS 2,004,714 A * 6/1935 Thompson .............. C07C 29/50
568/910.5
2,130,080 A 9/1938 Evans
(Continued)

FOREIGN PATENT DOCUMENTS

EP 0 407 038 B1 1/1995
WO 2008-135801 A2 11/2008

OTHER PUBLICATIONS

International Search Report dated Jul. 2, 2014 for PCT/US2014/027256 filed Mar. 14, 2014, 6 pgs.
(Continued)

*Primary Examiner* — Lessanework Seifu
(74) *Attorney, Agent, or Firm* — Brooks Kushman P.C.

(57) ABSTRACT

A method for forming a blend of ethers from a blend of alcohols includes a step of reacting a hydrocarbon-containing gas with an oxygen-containing gas to form first product blend. The first product blend includes a blend of partially oxygenated compounds. The blend of partially oxygenated compounds is provided to a reactive distillation station where it is converted a second product blend. The second product blend typically includes a mixture of ethers. An apparatus implementing the method is also provided.

8 Claims, 1 Drawing Sheet

Related U.S. Application Data 2014, now Pat. No. 9,745,238, which is a continuation of application No. 13/843,471, filed on Mar. 15, 2013, now abandoned.

(51) Int. Cl.
| | |
|---|---|
| *B01D 3/00* | (2006.01) |
| *C07C 29/50* | (2006.01) |
| *C07C 41/09* | (2006.01) |
| *B01J 12/00* | (2006.01) |
| *C07C 31/04* | (2006.01) |
| *C07C 31/08* | (2006.01) |
| *C07C 43/04* | (2006.01) |
| *C07C 43/06* | (2006.01) |

(52) U.S. Cl.
CPC .............. *C07C 29/50* (2013.01); *C07C 31/04* (2013.01); *C07C 31/08* (2013.01); *C07C 41/09* (2013.01); *C07C 43/04* (2013.01); *C07C 43/043* (2013.01); *C07C 43/06* (2013.01); *B01J 2208/00805* (2013.01); *Y02P 20/127* (2015.11)

(56) References Cited

U.S. PATENT DOCUMENTS

| | | | |
|---|---|---|---|
| 2,376,668 | A | 5/1945 | Derby et al. |
| 2,977,386 | A | 3/1961 | Kise et al. |
| 3,282,983 | A | 11/1966 | Lachowicz et al. |
| 4,065,421 | A | 12/1977 | Allyn et al. |
| 4,276,055 | A | 6/1981 | Huang |
| 4,417,903 | A | 11/1983 | Hinkamp |
| 4,541,835 | A | 9/1985 | Norton et al. |
| 4,541,837 | A | 9/1985 | Norton et al. |
| 4,603,662 | A | 8/1986 | Norton et al. |
| 4,618,451 | A | 10/1986 | Gent |
| 4,760,210 | A | 7/1988 | Sweeney |
| 4,833,171 | A | 5/1989 | Sweeney |
| 5,177,114 | A | 1/1993 | Van Dijk |
| 5,520,710 | A | 5/1996 | Olah |
| 5,628,805 | A | 5/1997 | Lif et al. |
| 6,013,114 | A | 1/2000 | Hille et al. |
| 6,255,357 | B1 | 7/2001 | Abbott |
| 6,270,541 | B1 | 8/2001 | Basu et al. |
| 6,486,362 | B1 | 11/2002 | Forestiere et al. |
| 6,514,299 | B1 | 2/2003 | Bean et al. |
| 6,548,681 | B1 | 4/2003 | Chopade et al. |
| 6,599,336 | B2 | 7/2003 | Hamada |
| 6,846,951 | B1 | 1/2005 | Thiebaut |
| 7,005,529 | B2 | 2/2006 | Eek-Vancells |
| 7,456,327 | B2 | 11/2008 | Pawlak et al. |
| 7,470,811 | B2 | 12/2008 | Thiebaut |
| 7,578,981 | B2 | 8/2009 | Pawlak et al. |
| 7,615,085 | B2 | 11/2009 | Schwab et al. |
| 7,642,293 | B2 | 1/2010 | Pawlak et al. |
| 7,687,669 | B2 | 3/2010 | Pawlak et al. |
| 7,846,978 | B2 | 12/2010 | Olah et al. |
| 7,879,296 | B2 | 2/2011 | Pawlak et al. |
| 7,910,787 | B2 | 3/2011 | Pawlak et al. |
| 8,148,589 | B2 | 4/2012 | Gracey et al. |
| 8,193,254 | B2 | 6/2012 | Pawlak et al. |
| 8,202,916 | B2 | 6/2012 | Pawlak et al. |
| 8,293,186 | B2 | 10/2012 | Pawlak et al. |
| 8,410,183 | B2 | 4/2013 | Cortright et al. |
| 9,174,903 | B2 | 11/2015 | Rao et al. |
| 9,255,051 | B2 | 2/2016 | Gaffney et al. |
| 9,587,189 | B2 | 3/2017 | Gaffney et al. |
| 2002/0026744 | A1 | 3/2002 | Golubkov et al. |
| 2006/0223892 | A1 | 10/2006 | Pawlak et al. |
| 2007/0100005 | A1 | 5/2007 | Pawlak et al. |
| 2007/0130822 | A1 | 6/2007 | Araya |
| 2009/0048468 | A1* | 2/2009 | Varkiani ................. C07C 41/09 568/671 |
| 2009/0069607 | A1 | 3/2009 | Smith, Jr. et al. |
| 2010/0041776 | A1 | 2/2010 | Czernichowski et al. |
| 2010/0158760 | A1 | 6/2010 | Pawlak et al. |
| 2010/0242347 | A1 | 9/2010 | Eberhard |
| 2011/0040129 | A1 | 2/2011 | Loescher |
| 2012/0142973 | A1 | 6/2012 | Su et al. |
| 2012/0232311 | A1 | 9/2012 | Hsieh et al. |
| 2013/0035519 | A1 | 2/2013 | Lee et al. |
| 2014/0275642 | A1 | 9/2014 | Rao et al. |
| 2014/0275643 | A1 | 9/2014 | Rao et al. |
| 2016/0031780 | A1 | 2/2016 | Gaffney et al. |
| 2016/0045890 | A1 | 2/2016 | Rao et al. |
| 2017/0145329 | A1 | 5/2017 | Gaffney et al. |

OTHER PUBLICATIONS

International Search Report dated Jul. 29, 2014 for PCT/US2014/028368 filed Mar. 14, 2014, 4 pgs.
International Search Report dated Aug. 22, 2014 for PCT/US2014/030161 filed Mar. 17, 2014, 4 pgs.
International Search Report dated Jan. 8, 2015 for PCT/US2014/058628 filed Jan. 1, 2015, 4 pgs.
Nunan, J.G. et al., "Methanol and 2-Methyl-1-Propanol (Isobutanol) Coupling to Ethers and Dehydration over Nafion H: Selectivity, Kinetics, and Mechanism," J. of Catalysis 139, 1993, pp. 406-420.
Zhang, X. et al, "Synthesis of Methylal by Catalytic Distillation," Chemical Engineering Research and Desigtn 89, 2011, pp. 573-580.
Kiernan, J.A. et al., "Formaldehyde, Formalin, Paraformaldehyde and Glutaraldehyde: What They Are and What They Do," Microcopy Today, 2000, pp. 8, 10, and 12 (pp. 9 and 11 omitted because they are advertisements).

* cited by examiner

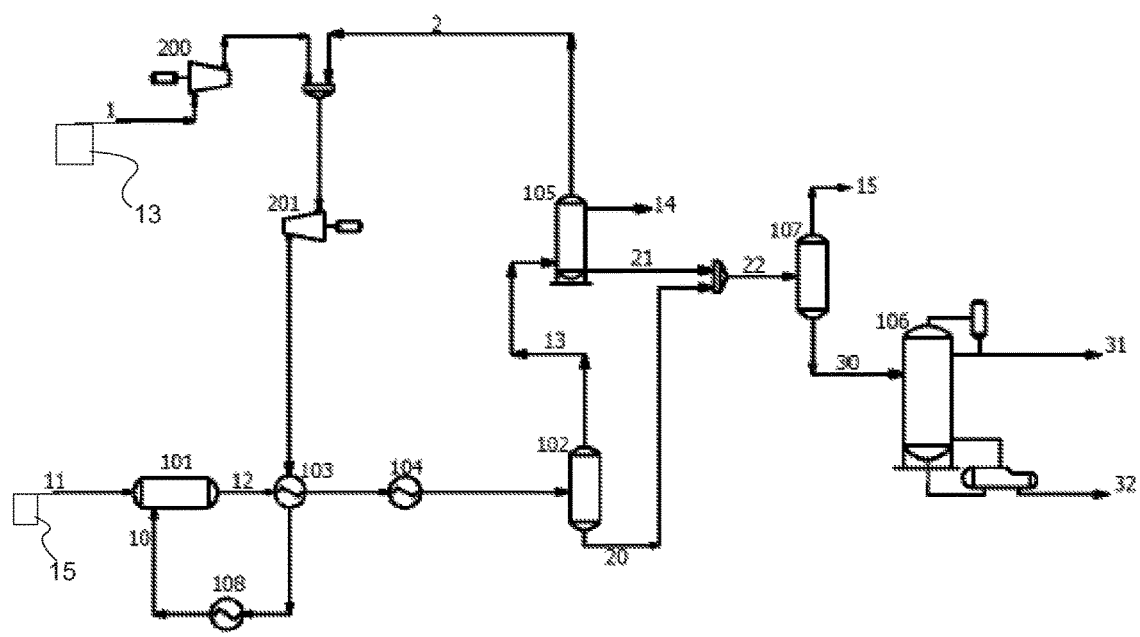

ETHER BLENDS VIA REACTIVE DISTILLATION

CROSS-REFERENCE TO RELATED APPLICATIONS

This application is a division of U.S. patent application Ser. No. 14/777,022 filed Sep. 15, 2015, now U.S. Pat. No. 9,745,238 issued Aug. 29, 2017, which is the U.S. national phase of PCT Application No. PCT/US2014/028368 filed Mar. 14, 2014, which is a continuation-in-part of to U.S. Ser. No. 13/843,471 filed Mar. 15, 2013, now abandoned, the disclosures of which are incorporated in their entirety by reference herein.

TECHNICAL FIELD

In at least one aspect, the present invention relates to methods and equipment for partially oxidizing a hydrocarbon feed gas.

BACKGROUND

Currently, direct homogeneous partial oxidation (DHPO) produces a variety of oxygenates typically consisting of alcohols and aldehydes, and in smaller concentrations carboxylic acids. Conversion of these liquid products into higher value fuels and chemicals via process integration is of great interest since process integration permits for cost reduction and therefore applicability at smaller scale.

The presented invention incorporates a gas to chemicals process with alcohol dehydration to produce dimethyl ether or an ether blend which presents more favorable properties for use as a diesel fuel substitute and additive. Advantages of process integration include the utilization of high temperatures and pressures already used by the gas to chemicals process, thus decreasing energy and equipment demands. Integration of a reactive distillation column thus facilitates separation of liquid products from the gas-to-chemicals process and also synthesizes a product of greater value.

Increasing the carbon length of the alkane feed gas is known to produce higher proportions of alcohols, aldehydes and carboxylic acids with carbon length greater than one. Many of these components have relative volatilities at standard temperature and pressure similar to that of water, complicating separations with conventional techniques. Furthermore, formaldehyde reversibly forms methylene glycol polymers that can interfere with recovery of high boiling alcohols. Therefore, there exists a need to efficiently separate these components, preferably as a readily usable product.

Pure methane gas, on the other hand, subjected to the direct homogeneous partial oxidation process produces primarily formaldehyde, methanol, and ethanol. Methanol is known, in the presence of certain catalysts, to undergo dehydration to DME. Furthermore, methanol is known to cleanly separate from a solution of higher alcohols and water under conventional distillation with reflux. In addition, ethanol is known to form an azeotrope with formaldehyde, allowing for the formaldehyde to remain with the ethanol and water as a polymerization inhibited blend. Through this property, the composition of oxygenates created by the DHPO process, upon removal of methanol, is sufficient for a commercial formalin blend. In the context of a reactive distillation column, aqueous formaldehyde is separated into formaldehyde gas and liquid water to generate an overhead product consisting of dialkyl ethers and formaldehyde gas and bottoms product composed of water.

As previously mentioned, feed gasses with a higher average molecular weight of alkane content than methane are known to produce higher carbon chain length alcohols as well as acids with correspondingly lower volatility. Methanol is also known to form dimethyoxymethane (methylal) in an acid catalyzed reaction with methanol and formaldehyde. In particular, sulfonic acid polymers such as Nafion® and Amberlyst® can catalyze such reactions. Other alcohols are known to form similar analogs. Said acid catalysts are also known to esterify carboxylic acids to esters and alcohols to ethers. This transformation eliminates the aldehyde azeotropes and increases the volatility of the mixture.

Dimethyl ether is known to be a substitute and blending additive for LPG and potentially diesel. It is also an intermediate in the synthesis of higher-value chemicals as well as gasoline. Dimethoxymethane as well as other dialkyl ethers exhibit similar properties with improved utility as a diesel substitute or oxygenate. Processing options include the removal of formaldehyde prior to reactive distillation. This may be achieved by reacting formaldehyde with different chemicals to produce compounds easily separated from the liquid mixture, eg. formaldehyde may react with urea to produce urea-formaldehyde. In this case, alcohols are easily separated from water and the formaldehyde-based component. Dehydration of the alcohol fraction (methanol and ethanol) would therefore result in an ether blend which presents characteristics that make the ether blend a more attractive diesel substitute or blending additive than DME alone.

Accordingly, there is a need for improved methods of making blends of ethers and other partially oxygenated compounds.

SUMMARY

The present invention solves one or more problems of the prior art by providing in at least one aspect an apparatus that uses reactive distillation to create a mixed alkyl ether product with formaldehyde gas in the overhead and water in the bottoms. Advantageously, the blend of ethers is a value added product that may be used to make other useful compositions such as a diesel fuel substitute or blending additive or an LPG blending additive.

In another aspect, an apparatus that uses reactive distillation to create an ether such as dimethyl ether (DME), and an ester blend in the overhead and treated water in the bottoms.

In yet another aspect, a method for forming a blend of ethers from a blend of partially oxygenated compounds is provided. The method includes a step of reacting a hydrocarbon-containing gas with an oxygen-containing gas in a reactor to form the first product blend. The first product blend includes a blend of partially oxygenated compounds. The blend of partially oxygenated compounds is provided through one or more conduits to a reactive distillation station where it is converted a second product blend. The second product blend typically includes a mixture of ethers.

In still another aspect, an apparatus for forming a blend of ethers from a blend of partially oxygenated compounds. The apparatus includes a reactor for reacting a hydrocarbon-containing gas with an oxygen-containing gas to form first product blend. The first product blend includes a blend of partially oxygenated compounds. A reactive distillation station is in fluid communication with the reactor. The reactive distillation station receives and converts the blend of partially oxygenated compounds to a second product blend at the reactive distillation station. The second product blend typically includes a mixture of ethers.

BRIEF DESCRIPTION OF THE DRAWINGS

FIG. 1 is a schematic illustration of a system for forming a blend of ethers using a reactive distillation component.

DETAILED DESCRIPTION

As required, detailed embodiments of the present invention are disclosed herein; however, it is to be understood that the disclosed embodiments are merely exemplary of the invention that may be embodied in various and alternative forms. The figures are not necessarily to scale; some features may be exaggerated or minimized to show details of particular components. Therefore, specific structural and functional details disclosed herein are not to be interpreted as limiting, but merely as a representative basis for teaching one skilled in the art to variously employ the present invention.

With reference to FIG. 1, a process and related apparatus for converting a blend of alcohols to a blend (i.e., a mixture) of ethers reactive distillation. In a refinement, the apparatus functions in a continuous manner when in operation. In a refinement, a blend of $C_{1-10}$ alcohols is converted to a blend of $C_{2-20}$ ethers. In another refinement, a blend of $C_{1-4}$ alcohols is converted to a blend of $C_{2-8}$ ethers. Examples of suitable alcohols include, but are not limited to, methanol, ethanol, propanols (e.g., n-propanol, iso-propanol), butanols (e.g., sec-butanol, tert-butanol, iso-butanol), pentanols, and combinations thereof, and the like. Examples of ethers in the blend of ethers include, but are not limited to, dimethyl ether, diethyl ether, methylethyl ether, dipropyl ether, methyl propyl ether, ethyl propyl ether, dipropyl ether, methyl butyl ether, propylbutyl ether, dibutylyether, and the like. As used herein, butyl and propyl include all isomers of these functional groups. In a further refinement, a blend of methanol and ethanol are converted to a blend of dimethyl ether, ethylmethyl ether, and diethyl ether. In a variation, when operating, the apparatus produces the blend of alcohols in a continuous fashion while continuously providing (i.e., flowing) the alcohol blend to reactive distillation station 106. The blend of ethers is formed in reactive distillation station 106. The blend of alcohols is produced by a gas-to-chemicals process in which a reactant stream including the hydrocarbon-containing gas composition 10 from hydrocarbon-containing source 13 is partially oxidized by an oxygen containing gas 11 from oxygen-containing source 15 to form first product stream 12. In a refinement, the reaction is operated at pressures from about 450 to 1250 psia and temperatures from about 350 to 450° C. The hydrocarbon-containing gas composition and the oxygen containing gas are each flowed to reactor 101. Examples of systems and methods of performing the partial oxidation as set forth in U.S. Pat. Nos. 8,293,186; 8,202,916; 8,193,254; 7,910,787; 7,687,669; 7,642,293; 7,879,296; 7,456,327; and 7,578,981; the entire disclosures of which are hereby incorporated by reference. In a refinement, the hydrocarbon-containing gas includes $C_{1-10}$ alkanes. In another refinement, the hydrocarbon-containing gas includes an alkane selected from the group consisting of methane, ethane, propanes, butanes, pentanes and combinations thereof. In another refinement, the hydrocarbon-containing gas includes an alkane selected from the group consisting of methane, ethane, and combinations thereof. Examples of oxygen containing gas include molecular oxygen which may be in the form of concentrated oxygen or air.

Following partial oxidation reaction, the product stream 12 is provided to and rapidly cooled in a series of heat exchangers 103 and 104 to prevent decomposition of the produced oxygenates and for separation of the liquid fraction (i.e., the alcohols in the blend of alcohols). Reactor 101 is in fluid communication with heat exchangers 103 and 104. After cooling product stream 12 at the heat exchangers, the formed liquids are separated from the gas stream at separation station 102. The gas stream is then provided to purification station 105 where a separation process for removal of non-hydrocarbon fractions from hydrocarbon fractions is performed. Purification station 105 may remove the non-hydrocarbon fractions by scrubbing, membrane separation, adsorption processes, cryogenic separations, or by purging a small gas fraction. The hydrocarbon fraction is then optionally recycled back to the reactor 101 with the intent of maximizing efficiency of the process.

Liquids generated by the gas-to-chemicals process are composed predominantly of alcohols and aldehydes, more specifically methanol, ethanol and formaldehyde. Basic separation of alcohols from a formalin solution is performed by simple fractional distillation. These streams may then be subjected to further separation processes for acquiring individual products at their desired purities. Because the gas-to-chemicals process operates at high pressures, there is no need for re-pressurization of the liquid stream for DME synthesis.

The present embodiment advantageously uses reactive distillation station 106 for conversion of the blend of alcohols to second product blend including ethers, and in particular, $C_{2-20}$ ethers. In a refinement, the second product blend includes a component selected from the group consisting of $C_{2-10}$ esters, methylene glycol ethers, and combinations thereof. In a refinement, the second product blend also includes formaldehyde. Reactive distillation station 106 is in fluid communication with reactor 101 as well as heat exchangers 103 and 104. In particular, the present embodiment uses reactive distillation for the conversion of a methanol or a methanol/ethanol blend to dimethyl ether or an ether blend resulting from dehydration of both methanol and ethanol fractions. In a refinement, in order to prevent formaldehyde from vaporizing in the distillation column bottom, it may be beneficial to remove formaldehyde prior to reactive distillation. This may be accomplished by using a selective scrubbing solution or a reactive scrubbing solution for either the aldehyde or alcohol fraction in station 107. In a refinement, catalyst station 107 operates at pressures of 10 to 200 psia, more preferably 50 to 150 psia, and at temperatures of 50 to 300° C. more preferably 150 to 25° C. In another refinement, formaldehyde hydrates may be submitted to the reactive distillation column 106 together with the alcohol fraction. In still another refinement, station 107 includes the reactive scrubber of U.S. patent application Ser. No. 13/841,975, entitled "Reactive Scrubbing for Upgrading Product Value, Simplifying Process Operation and Product Handling" and filed Mar. 15, 2013; the entire disclosure of this application is hereby incorporated by reference.

In a variation, reactive distillation station 106 includes a catalyst-packed column where reactive distillation is performed. In a refinement, the reactive distillation is operating at pressures between 50 and 250 psi, preferably between 100 and 200 psi. The catalyst used in the packed column catalyzes the conversion of alcohols to ethers. In a refinement, the catalyst is an immobilized catalyst. Examples of such catalysts include, but are not limited to, aluminosilicate catalysts, copper modified alumina catalyst, combinations thereof and the like. At these elevated pressures the boiling point of methanol is increased to the preferred temperatures for alcohol dehydration, between 50 and 300° C. and preferably between 150 and 250° C. Temperatures may be controlled so as to dehydrate only the methanol fraction to DME, or the methanol and ethanol fraction to an ether blend. Ethers are obtained from the column distillate 31 and water from the column bottoms 32 when formaldehyde has been removed from the process stream 30 prior to reactive distillation. In a refinement, reactive distillation station 106 includes one or more adiabatic reactors or Radial flow adiabatic fixed bed reactors. Examples of suitable reactive distillation stations and adiabatic beds are commercially available from Dupont, Haldor Topsoe, and Toyo Engineering Corporation.

In certain variations, an aqueous formaldehyde solution (i.e., less than 37% formaldehyde in water) or formalin is present in process stream 30, formaldehyde will exit the reactive distillation column together with the ethers (e.g., DME or the ether blend) in the distillate 31. Therefore, in a refinement, downstream separation of DME or the ether blend from formaldehyde can then be performed for acquisition of pure products, as well as conversion to products of higher value.

While exemplary embodiments are described above, it is not intended that these embodiments describe all possible forms of the invention. Rather, the words used in the specification are words of description rather than limitation, and it is understood that various changes may be made without departing from the spirit and scope of the invention. Additionally, the features of various implementing embodiments may be combined to form further embodiments of the invention.

What is claimed is:

1. An apparatus for forming a blend of ethers from a blend of partially oxygenated compounds, the apparatus comprising:
    a) a reactor for reacting a hydrocarbon-containing gas with an oxygen-containing gas to form first product blend, the first product blend including a blend of partially oxygenated compounds that includes alcohols and aldehydes wherein the hydrocarbon-containing gas is reacted with the oxygen-containing gas at pressures from about 450 to 1250 psia and temperatures from about 350 to 450° C.; and
    b) a reactive distillation station in fluid communication with the reactor, the reactive distillation station receiving and converting the blend of partially oxygenated compounds to a second product blend at the reactive distillation station, the second product blend including a mixture of ethers and a component selected from the group consisting of $C_{2-10}$ esters, methylene glycol ethers and combinations thereof.

2. The apparatus of claim 1 wherein the reactive distillation station includes a catalyst packed column having a catalyst that converts alcohols to ethers.

3. The apparatus of claim 2 wherein the catalyst is selected from the group consisting of aluminosilicate catalysts, copper modified alumina catalyst, and combinations thereof.

4. The apparatus of claim 1 further comprising a first source that provides $C_{1-10}$ alkanes to the reactor as the hydrocarbon-containing gas.

5. The apparatus of claim 4 wherein the hydrocarbon-containing gas includes an alkane selected from the group consisting of methane, ethane, propanes, butanes, pentanes and combinations thereof.

6. The apparatus of claim 1 further comprising, a second source that provides oxygen to the reactor.

7. The apparatus of claim 1 wherein the second product blend includes a mixture of $C_{2-20}$ alkyl ethers.

8. The apparatus of claim 7 wherein the second product blend includes an ether selected from the group consisting of dimethyl ether, diethyl ether, methylethyl ether, dipropyl ether, methyl propyl ether, ethyl propyl ether, dipropyl ether, methyl butyl ether, propylbutyl ether, dibutylyether, and combinations thereof.

* * * * *